United States Patent
Cheng

(10) Patent No.: US 6,263,746 B1
(45) Date of Patent: Jul. 24, 2001

(54) SLOT ASSEMBLY TEST APPARATUS

(75) Inventor: Chieh-Fu Cheng, Taipei (TW)

(73) Assignee: Inventec Corporation, Taipei (TW)

( * ) Notice: Subject to any disclaimer, the term of this patent is extended or adjusted under 35 U.S.C. 154(b) by 0 days.

(21) Appl. No.: 09/287,347

(22) Filed: Apr. 7, 1999

(30) Foreign Application Priority Data

Aug. 6, 1998 (TW) .................................................. 87212845

(51) Int. Cl.[7] .................................................. G01N 19/00
(52) U.S. Cl. .................................................. 73/865.9
(58) Field of Search ........................ 73/865.9, 7

(56) References Cited

U.S. PATENT DOCUMENTS 5,447,072 * 9/1995 Holung ............................... 73/865.9

* cited by examiner

Primary Examiner—Hezron Williams
Assistant Examiner—Katina M Wilson
(74) Attorney, Agent, or Firm—Finnegan, Henderson, Farabow, Garrett & Dunner, L.L.P.

(57) ABSTRACT

The present invention provides a slot assembly test apparatus for testing a slot assembly having an ejection mechanism by means of a card. The slot assembly test apparatus comprises: a platform; a slot assembly fixture disposed on the platform for positioning the slot assembly in which the card has been inserted; a pushing device; and a touching device. The pushing device is disposed on the platform and capable of moving between a first position, at which the card is pushed by the first pushing device to a predetermined position, and a second position, at which the first pushing device is drawn away from the card. The touching device disposed on the platform is capable of touching the ejection mechanism of the slot assembly so as to eject the card from the slot assembly.

7 Claims, 3 Drawing Sheets

SLOT ASSEMBLY TEST APPARATUS

FIELD OF THE INVENTION

The present invention relates to a slot assembly test apparatus, and more particularly to a slot assembly test apparatus suitable for automatically testing the usage life-span of the slot assembly, in which the pushing in and ejecting of the PCMCIA card are conducted automatically.

DESCRIPTION OF PRIOR ART

Due to the convenience and portability of palmtop computers, for example electronic dictionaries, they have been widely adopted in our daily life. However, the memory of the palmtop computer is limited. Thus, a PCMCIA (Personal Computer Memory Card Industry Association) slot assembly can be mounted on the palmtop computer to receive a PCMCIA card and enhance the function of the palmtop computer.

The conventional procedure for testing the usage lifespan of a PCMCIA slot assembly is conducted manually and will be described as follows. First, operators push the PCMCIA slot card into the slot of the slot assembly. Then, the button on the slot assembly is pressed twice to eject the card out from the slot. The button usually is a two-stage button. That is to say, the card will not be ejected until the button is pressed twice. After the card is ejected and a few seconds pass, another cycle of pushing and ejecting the card is conducted. The testing cycle of pushing and ejecting the card is repeated continuously until the card can not be pushed into or ejected properly. The maximum number of properly conducted testing cycles indicates the usage life-span of the slot assembly.

However, the manually operated testing method for the slot assembly suffers from several problems. Since the PCMCIA card is pushed into and ejected by persons, the force applied to the card is not always the same for each testing cycle. Thus, the data obtained is not reliable and has less value. In addition, operators who do the slot assembly testing tend to suffer from occupational disease affecting their hands.

SUMMARY OF THE INVENTION

Therefore, an object of the present invention is to solve the above-mentioned problems and to provide a slot assembly test apparatus for testing the usage life-span of the slot assembly automatically rather than manually.

To achieve the above object, the present invention provides a slot assembly test apparatus for testing a slot assembly having an ejection mechanism by means of a card. The slot assembly comprises:

a platform;

a slot assembly fixture disposed on the platform for positioning the slot assembly in which the card has been inserted;

a pushing device disposed on the platform and capable of moving between a first position, at which the card is pushed by the first pushing device to a predetermined position in the slot assembly, and a second position, at which the first pushing device is drawn away from the card; and a touching device disposed on the platform and capable of touching the ejection mechanism of the slot assembly so as to eject the card out from the slot assembly.

BRIEF DESCRIPTION OF THE DRAWINGS

The present invention is hereinafter described in detail by the preferred embodiments with reference to the accompanying drawings wherein.

DETAILED DESCRIPTION OF THE PREFERRED EMBODIMENTS

Figure 1:
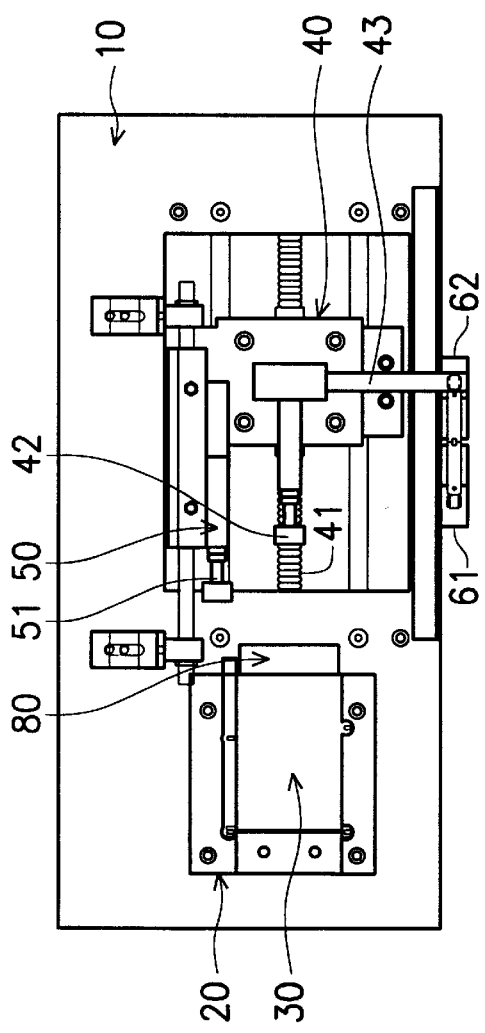
FIG. 1 is a top view showing the slot assembly test apparatus according to the present invention.
Figure 3:
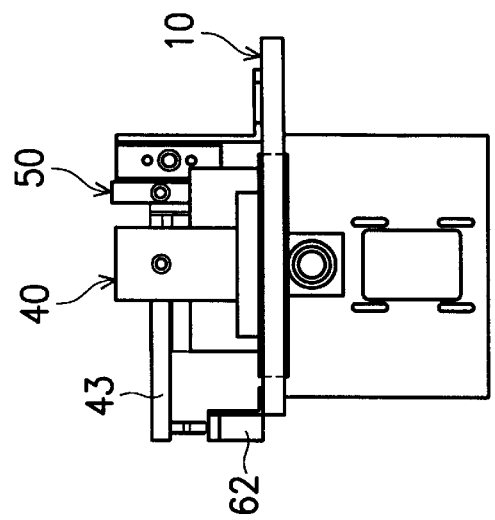
FIG. 3 is a side view showing the slot assembly test apparatus according to the present invention.
Figure 2:
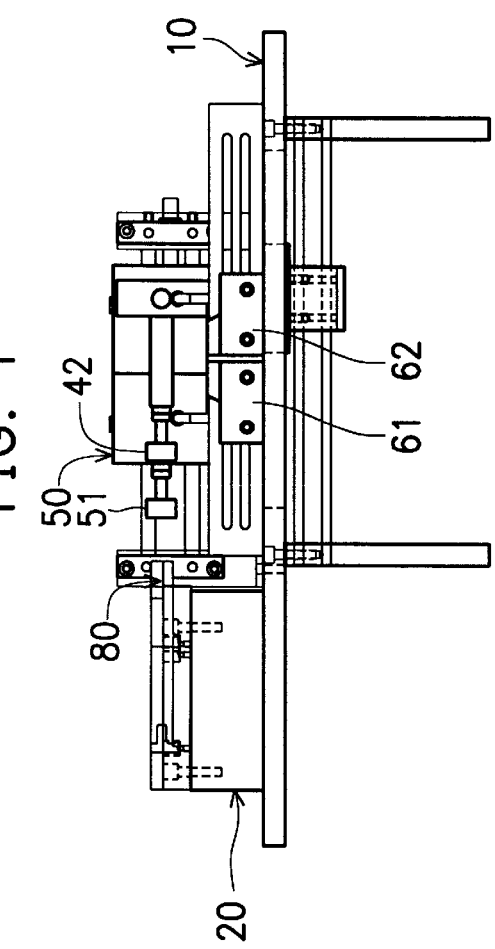
FIG. 2 is a front view showing the slot assembly test apparatus according to the present invention.

Referring to FIGS. 1 to 4, the slot assembly test apparatus according to the present invention includes a platform 10, a slot assembly fixture 20, a pushing device 40, and a touching device 50.

The slot assembly fixture 20 is disposed on the platform 10 for positioning a slot assembly 30 to be tested. The slot assembly 30 has a slot into which a card 80 can be inserted.

The pushing device 40 is disposed on the platform 10 and is capable of moving between a first position and a second position. At the first position, the card 80 is pushed by the first pushing device 40 into a predetermined position in the slot of the slot assembly 30. At the second position, the first pushing device 40 is away from the card 80. Preferably, the pushing device 40 is provided with a pushing block 42 for pushing the card 80 into a predetermined position of the slot assembly 30. A guide screw 41 is engaged with the pushing device 40.

The touching device 50, for example a sliding cylinder, is disposed on the platform and capable of touching an ejection mechanism of the slot assembly 30, exemplified as a button 31 in the figures, so as to eject the card 80 from the slot assembly 30. Preferably, the touching device 50 is provided with a pressing block 51 for pressing the button 31 of the slot assembly 30 so as to eject the card 80 from the slot assembly 30.

The slot assembly test apparatus further includes two microswitches 61 and 62 disposed on the platform for controlling the position of the pushing device 40. A controller 70 is coupled to the pushing device 40, the touching device 50, and the microswitches 61 and 62, respectively. The pushing device 40 is provided with a lateral rod 43 for actuating the microswitches 61 and 62.

Figure 4:
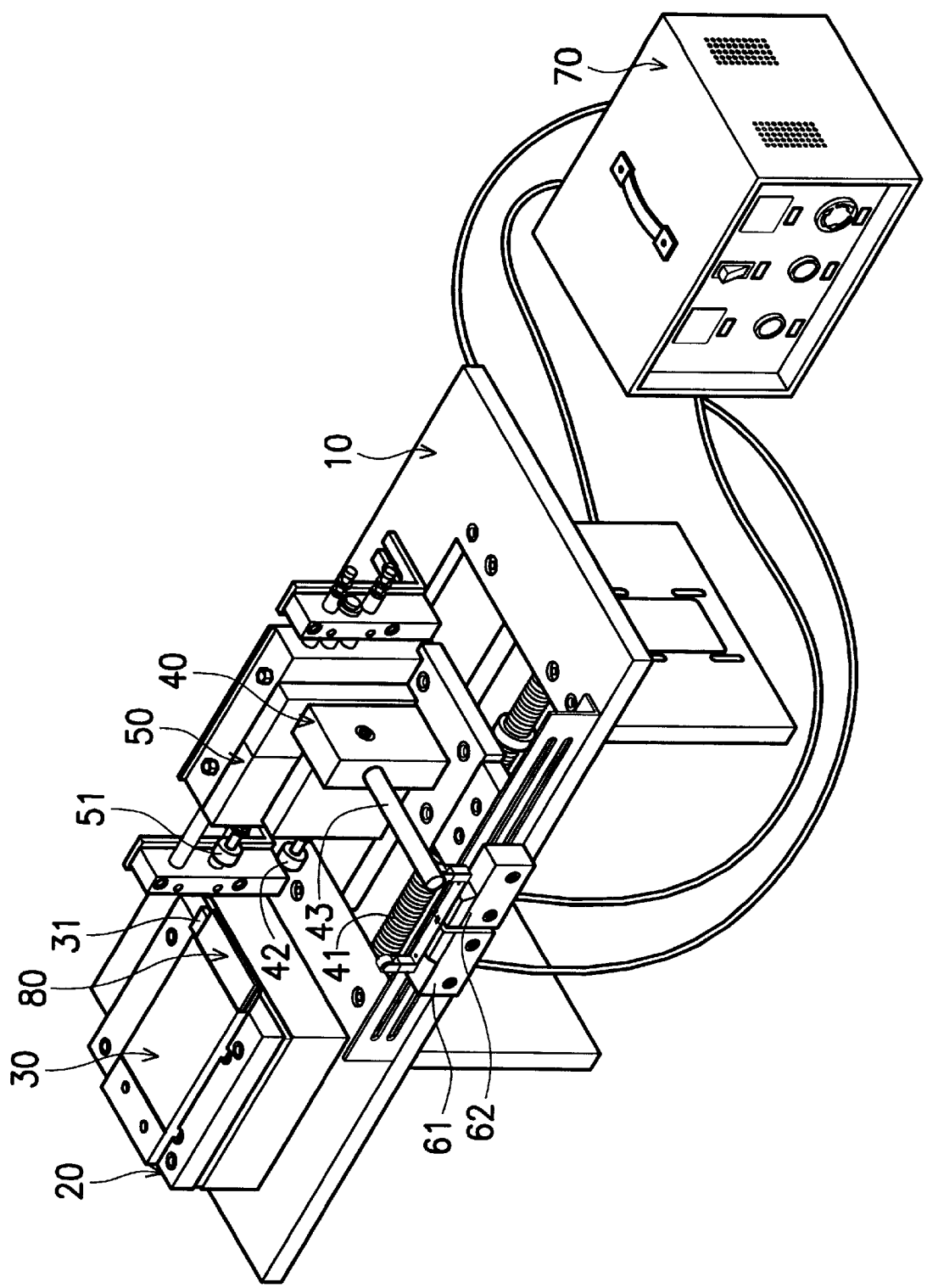
FIG. 4 is a perspective view showing the slot assembly test apparatus according to the present invention.
Figure 5:
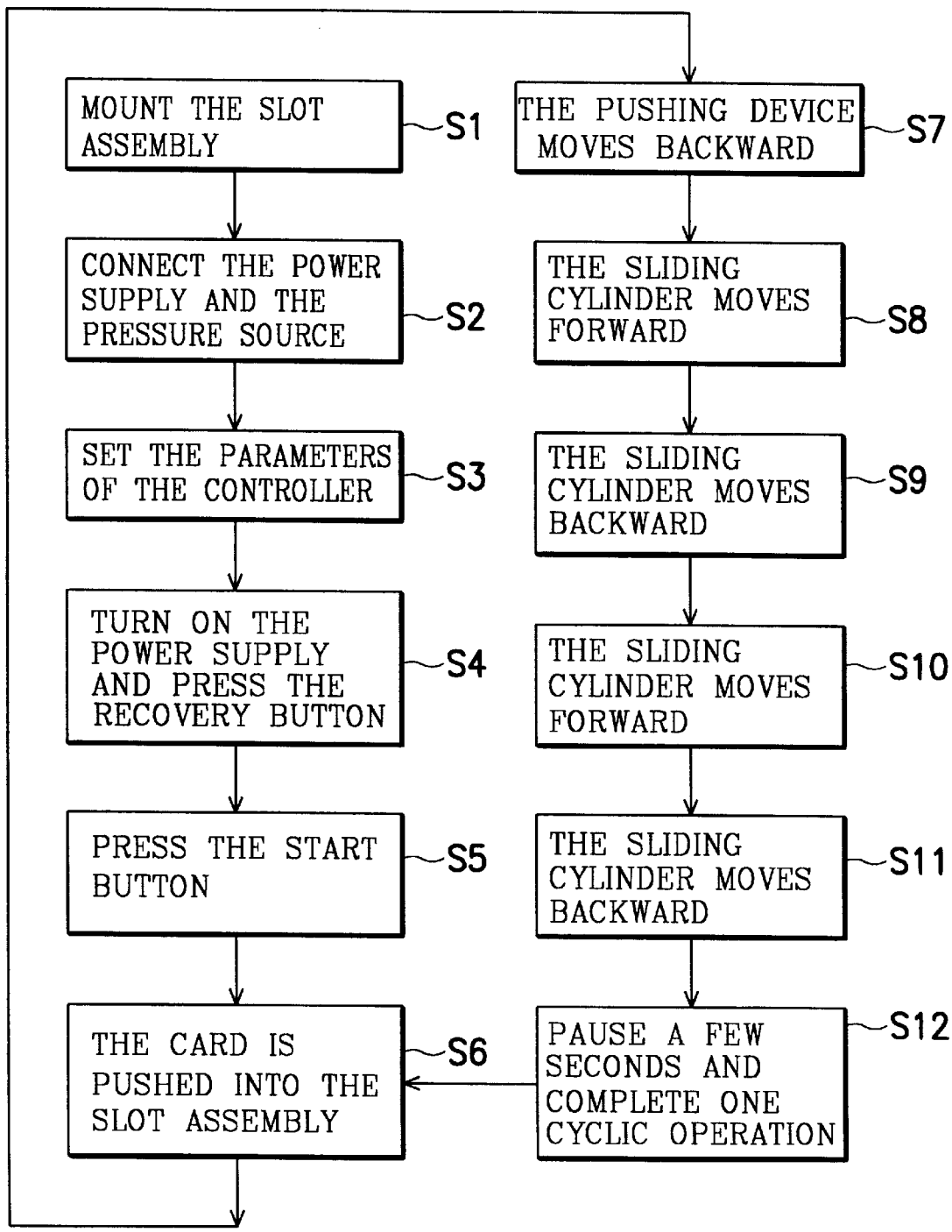
FIG. 5 is a flow chart showing the test process using the slot assembly test apparatus according to the present invention.

Referring to FIGS. 4 and 5, the test process of the slot assembly is explained as follows.

In S1, the slot assembly 30 is fixed on the slot assembly fixture 20. Then, the slot assembly fixture 20 is fixed on the platform 10, and the card 80 is positioned (not inserted) in the slot assembly 30.

In S2, the pressure duct of the platform 10 is connected to a pressure source in the factory. The platform 10 is also electrically connected to a power supply.

In S3, the parameters such as the rotation speed of the motor (not shown) for driving the pushing device 40 and that for driving the touching device 50 are set.

In S4, the power supply of the controller 70 is turned on. The recovery button of the controller 70 is also turned on to make the pushing device 40 return to its original position. At this position, the pushing block 42 is not in contact with the card 80 positioned in the slot of the slot assembly 30.

In S5, the start button of the controller 70 is pressed to actuate a motor to drive the guide screw 41 to rotate. By means of the rotation of the guide screw 41, the pushing device 40 moves forward.

In S6, the pushing device 40 moves forward until the pushing block 42 contacts the card 80 and pushes the card 80 into a predetermined position of the slot assembly 30. At this moment, the lateral rod 43 is in contact with the first microswitch 61. Then, the first microswitch 61 sends a signal to the controller 70.

In S7, when the controller 70 receives the signal from the first microswitch 61, it outputs a signal to the pushing device 40 to make the guide screw 41 reverse rotation. This makes the pushing device 40 move backward until the lateral rod 43 contacts the second microswitch 62.

In S8, the second microswitch 62 will send a signal to the controller 70. When the controller 70 receives the signal from the second microswitch 62, it outputs a signal to the sliding cylinder 50 to order the sliding cylinder 50 to move forward.

In S9, the sliding cylinder 50 moves forward until the pressing block 51 contacts button 31 and presses button 31 of the slot assembly 30; thus, the magnetic switch (not shown) in the button 31 is actuated. The magnetic switch outputs a signal to the controller 70. Then, the controller 70 transmits a signal to the sliding cylinder 50 to order the sliding cylinder 50 to move backward.

In S10, the backward movement of the sliding cylinder 50 will actuate another magnetic switch (not shown). This magnetic switch outputs another signal to the controller 70. Then, the controller 70 transmits a signal to the sliding cylinder 50 to order the sliding cylinder 50 to move forward again. In S11, the sliding cylinder 50 moves forward until the pressing block 51 contacts button 31 and presses button 31 of the slot assembly 30 again. This second time of pressing will cause the PCMCIA card 80 to eject and cause a magnetic switch (not shown) to actuate. The magnetic switch outputs a signal to the controller 70. Then, the controller 70 transmits a signal to the sliding cylinder 50 to order the sliding cylinder 50 to move backward again.

In S12, after the sliding cylinder 50 moves backward, one cycle of the testing operation is completed. The controller 70 counts once. After pausing for a few seconds, the controller 70 outputs a signal to drive the guide screw 41 to rotate, thus making the pushing device 40 move forward. This is the beginning of another cycle of the testing operation. Steps S6 to S12 are repeated until the test is completed.

In general, the procedures of pushing and ejecting the PCMCIA card continue until the card can not be pushed or ejected properly anymore. The maximum numbers of properly operated testing cycle indicates the usage life-span of the slot assembly.

As a result, the slot assembly test apparatus of the present invention has the following advantages:

(1) The PCMCIA card is pushed into the slot assembly by a constant force, which will not change even after many cycles of testing operation.

(2) Since the pushing and ejecting of the PCMCIA card are conducted automatically, the data obtained are much more reliable and valuable than those obtained by using a conventional test apparatus in which the pushing and ejecting of the PCMCIA card are conducted manually.

(3) Manpower can be saved, and operators who test the life of use of the slot assembly can avoid the occupational disease due to pushing and ejecting the PCMCIA card manually.

What is claimed is:

1. A slot assembly test apparatus for testing a slot assembly having an ejection mechanism by means of a card, comprising:

a platform;

a slot assembly fixture disposed on the platform for positioning the slot assembly in which the card has been inserted;

a pushing device disposed on the platform and capable of moving between a first position, at which the card is pushed by the first pushing device to a predetermined position in the slot assembly, and a second position, at which the first pushing device is drawn away from the card;

two microswitches disposed on the platform for controlling the position of the pushing device; and a touching device disposed on the platform and capable of touching the ejection mechanism of the slot assembly so as to eject the card out from the slot assembly.

2. The slot assembly test apparatus as claimed in claim 1, wherein the pushing device is provided with a pushing block for pushing the card to a predetermined position of the slot assembly.

3. The slot assembly test apparatus as claimed in claim 1, wherein the touching device is provided with a pressing block for pressing the ejection mechanism of the slot assembly so as to eject the card out from the slot assembly.

4. The slot assembly test apparatus as claimed in claim 1, wherein the touching device is a sliding cylinder.

5. The slot assembly test apparatus as claimed in claim 1, wherein the ejection mechanism comprises a button.

6. The slot assembly test apparatus as claimed in claim 1, further comprising a controller coupled to the pushing device, the touching device, and the microswitches, respectively.

7. The slot assembly test apparatus as claimed in claim 1, wherein the pushing device is provided with a lateral rod for actuating the microswitches.

* * * * *